(12) United States Patent
Okada et al.

(10) Patent No.: US 7,241,809 B2
(45) Date of Patent: Jul. 10, 2007

(54) METHOD FOR TREATING INFLAMMATORY BOWEL DISEASES

(75) Inventors: Yoshikiyo Okada, Tokorozawa (JP); Yoshikazu Tsuzuki, Tokorozawa (JP); Soichiro Miura, Tokorozawa (JP)

(73) Assignees: Meiji Dairies Corporation, Tokyo (JP); The Food Science Institute Foundation, Odawara-shi (JP)

(*) Notice: Subject to any disclaimer, the term of this patent is extended or adjusted under 35 U.S.C. 154(b) by 346 days.

(21) Appl. No.: 10/740,675

(22) Filed: Dec. 22, 2003

(65) Prior Publication Data

US 2005/0137261 A1 Jun. 23, 2005

(51) Int. Cl.
*A61K 31/192* (2006.01)
(52) U.S. Cl. .................................................. 514/559
(58) Field of Classification Search ............... None
See application file for complete search history.

(56) References Cited

U.S. PATENT DOCUMENTS

2004/0241815 A1* 12/2004 Sato et al. ............... 435/136

2005/0137261 A1 6/2005 Okada et al. ............ 514/569

OTHER PUBLICATIONS

The Merck Manual, 17th edition, 1999, pp. 302-312, & 313.*
Yoshikiyo Okada, et al. "Studies of Antiinflammatory Effect of DHNA, a Component of Whey Fermentation Product, Produced by Propionic Acid Bacterium on DSS Enteritis", 40th Annual Meeting of Japanese Society for Mucosal Immunology, Aug. 7 and 8, 2003, 3 pgs (with Translation).
Yoshikiyo Okada "Studies of Antiinflammatory Effect of DHNA, a Component of Whey Fermentation Product, Produced by Propionic Acid Bacterium on DSS Enteritis", The 89th Annual Meeting of the Japanese Society of Gastroenterology, Apr. 24 to 26, 2003, 5 pgs (with Translation).
Y. Okada, et al., "*Propionibacterium freudenreichii* Component 1.4-Dihydroxy-2-Naphthoic Acid (DHNA) Attenuates Dextran Sodium Sulphate Induced Colitis by Modulation of Bacterial Flora and Lymphocyte Homing", Gut 2006:55:681-688.

* cited by examiner

*Primary Examiner*—Phyllis G. Spivack
(74) *Attorney, Agent, or Firm*—Oblon, Spivak, McClelland, Maier & Neustadt, P.C.

(57) ABSTRACT

The present invention relates to a method for treating an inflammatory bowel disease, including administering an effective amount of 1,4-dihydroxy-2-naphthoic acid or a salt thereof.

14 Claims, 3 Drawing Sheets

H&E staining of colonic mucosa

DSS          DSS+DHNA(0.6mg/kg)    DSS+DHNA(2.0mg/kg)

β 7 integrin positive cells in murine colonic mucosa

DSS    DSS+DHNA(0.6mg/kg)    DSS+DHNA(2.0mg/kg)

Number of β7 positive cells in colonic mucosa

Expression of MAdCAM-1 in murine colonic mucosa

DSS      DSS+DHNA(0.6mg/kg)      DSS+DHNA(2.0mg/kg)

Expression of MAdCAM-1 in colonic mucosa

: $p < 0.05$ vs.control

US 7,241,809 B2

METHOD FOR TREATING INFLAMMATORY BOWEL DISEASES

BACKGROUND OF THE INVENTION

1. Field of the Invention

The present invention relates to a method for treating inflammatory bowel diseases such as ulcerative colitis and Crohn's disease.

2. Background Art

Inflammatory bowel disease is the name of a group of chronic inflammation or ulceration of the mucosae of the large and small intestines of unknown cause. Ulcerative colitis and Crohn's disease are two representative diseases.

In some reports, immune regulation for enteric bacteria or food antigens is suggested as possible causes of inflammatory bowel disease. However, no clear elucidation has currently been established.

Therapeutic agents for inflammatory bowel disease, and for ulcerative colitis in particular, include salazosulfapyridine, 5-aminosalicylic acid, steroids, and immunosuppressors. However, these agents provide limited therapeutic effects, and moreover, steroids and immunosuppressors create serious problems of adverse side effects after long-term administration.

SUMMARY OF THE INVENTION

An object of the present invention is to provide a highly safe method for treating or preventing inflammatory bowel diseases such as ulcerative colitis and Crohn's disease.

To achieve this object, the present inventors have performed extensive research, and has found that 1,4-dihydroxy-2-naphthoic acid or a salt thereof improves mucosal inflammation of intestinal bowel disease, and suppresses invasion of activated immunocytes.

Accordingly, the present invention provides a method for treating inflammatory bowel diseases, characterized by administering an effective amount of 1,4-dihydroxy-2-naphthoic acid or a salt thereof to a patient in need thereof.

The present invention provides safe measures in the prevention or treatment of inflammatory bowel diseases.

DETAILED DESCRIPTION OF THE INVENTION AND PREFERRED EMBODIMENTS

Figure 1:
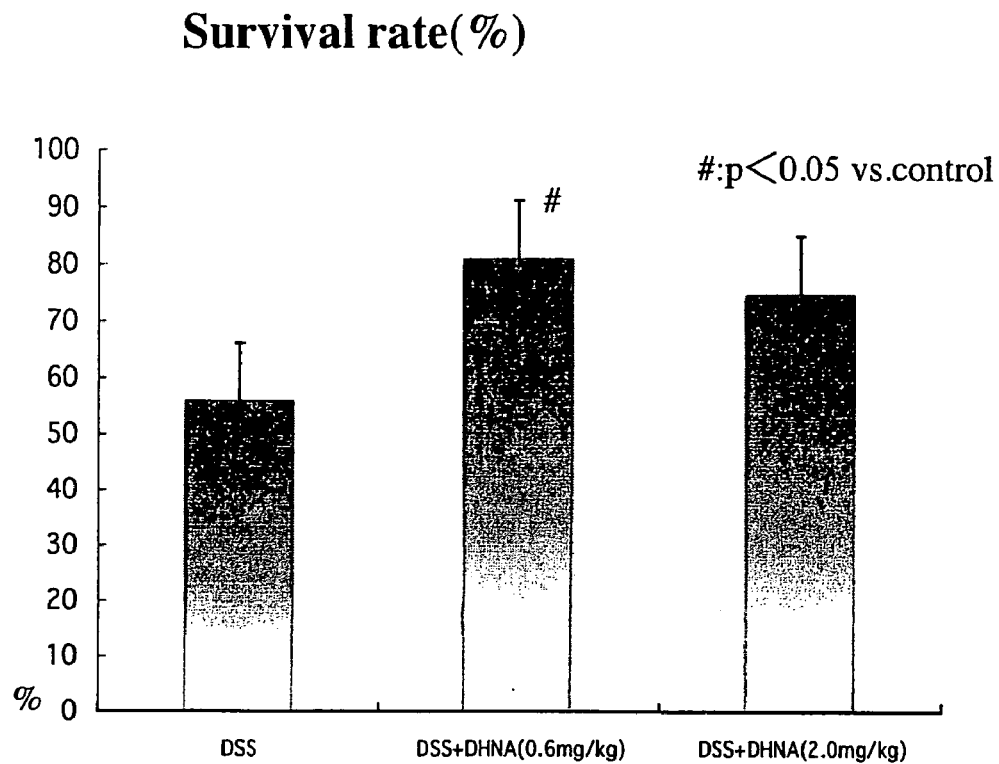
FIG. 1 shows survival rates of rats with DSS colitis as found under conditions with or without administration of DHNA.

The active agent of the treatment method of the present invention is 1,4-dihydroxy-2-naphthoic acid (DHNA) or a salt thereof. DHNA and its salts have heretofore been known to find utility in dyes, pigments, and photosensitive materials. WO03/016544 teaches that DHNA or its salts mitigate abdominal discomfort experienced by a subject of milk intolerance after ingestion of milk and that they are useful in the prevention or treatment of metabolic bone diseases. WO03/016544 also teaches that propionic acid bacteria produce large amounts of DHNA inside and outside of the cells and that DHNA exhibits an action of stimulating proliferation of *Bifidobacterium bifidum*. However, these documents are silent about modes of actions of DHNA or its salts exerted on inflammatory bowel diseases.

DHNA and its salts can be prepared through a chemical synthesis technique known per se. Preferably, they are prepared through fermentation of propionic acid bacteria.

No particular limitation is imposed on specific identities of the propionic acid bacteria which can be used for producing DHNA, so long as they are DHNA-producing microorganisms. However, microorganisms belonging to genus *Propionibacterium* are preferred. For example, mention may be given of microorganisms used for producing cheeses, such as *Propionibacterium freudenreichii*, *Propionibacterium thoenii* (*P. thoenii*), *Propionibacterium acidipropionici* (*P. acidipropionici*), *Propionibacterium jensenii* (*P. jensenii*); and *Propionibacterium avidum* (*P. avidum*), *Propionibacterium acnes* (*P. acnes*), *Propionibacterium lymphophilum* (*P. lymphophilum*), and *Propionibacterium granulosam* (*P. granulosam*). Of these, *Propionibacterium freudenreichii* is preferred, with *P. freudenreichii* IFO 12424, *P. freudenreichii* ATCC 6207, and *P. freudenreichii* ET-3 (FERM P-18454) being particularly preferred.

Examples of media employable for the fermentation of the propionic acid bacteria include those containing whey powder, casein, skim milk, whey protein concentrate, or whey protein derivative, yeast extract, peptone such as trypticase; glucose, lactose or lactase-treated product of lactose, and whey minerals; i.e., media containing suitable amounts of sugars and minerals. Preferably, culture conditions are 20 to 40° C. and neutral to slightly acidic (pH 5.5 to 7.5).

Next an explanation will be given of how DHNA is collected from the culture product. Preferably, adsorption chromatography is applied to the obtained culture product. As an adsorbent, there may be used a wide range of adsorbents generally used in reverse phase chromatography, such as activated carbon and synthetic adsorbent (e.g., DIAION HP-20, produced by Mitsubishi Chemical Corporation). Firstly, the column is packed with the adsorbent, and washed with 0.5-w/v % aqueous sodium ascorbate solution. Next, the obtained culture product is added to the column (the solution that has passed through the column will be referred to as "pass"). By use of 0.5-w/v % aqueous sodium ascorbate solution, the water-soluble fraction is removed. Subsequently, the column is eluted with ethanol to which 0.5-w/v % sodium ascorbate has been added, and when this ethanol-eluted fraction is concentrated, a composition containing DHNA at a high concentration can be obtained. The composition is further purified, whereby pure DHNA or a salt thereof can be obtained. In this connection, the eluant for DHNA may be methanol instead of ethanol.

Salts of DHNA may be pharmacologically acceptable salts and salts that are acceptable in view of food science. Typical examples of such salts include, but are not limited to, acetates, benzenesulfonates, benzoates, hydrogencarbonates, lactates, and citrates.

DHNA is contained in a culture product of a DHNA-producing microorganism (inside and/or outside the cells). Therefore, without use of adsorption chromatography, the culture product itself may be concentrated by use of a rotary evaporator or a similar device, whereby a composition containing DHNA at a high concentration can be obtained. In an alternative method which is also preferred, cells are separated from the culture product by means of a customary centrifugal separation technique and the thus-collected supernatant is concentrated. The thus-obtained composition may be used as is; in other words, in the form of liquid, or processed into a powder before use, whichever is preferred in accordance with the mode of application.

As will be described in the Example section provided hereinbelow, DHNA and its salts have been found to have excellent preventive and therapeutic action against dextran sodium sulfate (DSS) colitis, which is a well-known model of inflammatory bowel disease. Specifically, DHNA and its salts have been found to suppress epithelial ulceration or erosion, which are typical pathological profiles of DSS colitis, and also suppress submucosal cellular infiltration and submucosal thickening. Also, following administration of DHNA or a salt thereof, reduction in β7 positive cell count and suppressed expression of MAdCAM-1 were observed. Therefore, conceivably, the effect of DHNA and its salts on inflammatory bowel disease is derived from suppression of invasion of activated immunocytes.

Examples of the inflammatory bowel disease serving as the target of the treatment according to the present invention include ulcerative colitis and Crohn's disease.

DHNA or a salt thereof may be used in any form of food, beverage, or drug. For example, it may be directly administered as a drug. Alternatively, a subject may directly ingest it in the form of food, such as food for specified health use falling under "foods for special dietary use" or nutritive functional food. The inflammatory bowel disease may also be treated in the following manner: DHNA or a salt thereof is added to any of a variety of foods (such as milk, soft drink, fermented milk, yogurt, cheese, bread, biscuit, cracker, and pizza crust), and the patient ingests the resultant food.

In the manufacture of the above-described foods, various predominant components may be used in combination, such as water, proteins, saccharides, lipids, vitamins, minerals, organic acids, fruit juice, and flavors. For example, there may be employed animal or vegetable proteins such as whole milk powder, skim milk, partially skimmed milk, casein, whey powder, whey protein, whey protein concentrate, separated components of whey protein, α-casein, β-casein, β-lactoglobulin, α-lactalbumin, lactoferrin, soybean protein, egg protein, and meat protein; hydrolysates thereof; a variety of milk-derived components such as butter, cream, whey, whey mineral, non-protein nitrogen, sial acid, phospholipids, and lactose; carbohydrates such as sucrose, glucose, fructose, sugaralcohol, maltose, oligosaccharides, chemically processed starch (dextrin, soluble starch, British starch, oxidized starch, starch ester, and starch ether), and dietary fiber; animal oils and fats such as lard and fish oil; vegetable oils and fats such as palm oil, safflower oil, corn oil, rape seed oil, and coconut oil; and fractionated oils, hydrogenated oils, and transesterificated oils derived from these vegetable oils or fats; vitamins such as vitamin A, those belonging to the vitamin B group, vitamin C, those belonging to the vitamin D group, vitamin E, those belonging to the vitamin K group, vitamin P, vitamin Q, niacin, nicotinic acid, pantothenic acid, biotin, inositol, choline, and folic acid; minerals such as calcium, potassium, magnesium, sodium, chlorine, copper, iron, manganese, zinc, selenium, fluorine, silicon, and iodine; and organic acids, such as malic acid, citric acid, lactic acid, tartaric acid, and salts thereof. From among these members, one or more ingredients may be appropriately selected and incorporated. Preferably, any of these ingredients may be incorporated in the form of a synthetic product, or instead, food containing any of these ingredients at a significant proportion may be employed.

When DHNA or a salt thereof is used as a drug, such a drug may be administered in a variety of forms. Examples of such forms include tablets, capsules, granules, powders, and syrups, which are administered through the oral route. These drug formulations may be processed in accordance with a customary method using, in addition to the active agent, known adjuvants which are ordinarily used in the technical field of drug preparation, such as excipients, binders, disintegrants, lubricants, sweetening agents, flavoring agents, solubilizers, suspending agents, and coating agents.

Preferably, the typical daily dose of DHNA or a salt thereof is 1 to 100 mg for an adult.

EXAMPLE

The present invention will next be described in more detail by way of example, which should not be construed as limiting the invention thereto.

Example 1

A. Materials and Methods (Test Animals)

C57/BL6 Mice (female, 8 weeks old) were employed. They were bred under SPF conditions, and then used in the test.

(Induction of Colitis and DHNA Administration Method)

2.5% Dextran sodium sulfate (DSS, MW 50,000) was added to drinking water (distilled water) for mice, and the mice were allowed to drink the resultant water freely for 7 days (induction of colitis). Subsequently, DHNA was administered to the mice in the following manner.

DHNA was dissolved in dimethyl sulfoxide (DMSO) (0.1 g/0.5 mL). The resultant neat solution, along with ascorbic acid for stabilizing DHNA (1%), was added to drinking water (distilled water) for mice, and the mice were allowed to drink the resultant water freely for 7 days. DHNA concentration was 0.6 mg/kg or 2 mg/kg. Distilled water to which DMSO and ascorbic acid had been added in equal amounts was employed as a control group.

(Items of Examination)

(1) Survival Rate

Survival rate was that as determined for the mice on day 10 after starting administration of DHNA.

(2) Histological Examinations

The large intestine was removed from each mouse, and fixed with periodate-lysine-paraformaldehyde (PLP), whereby frozen slices were prepared. Through use of the thus-obtained frozen sections, immunohistochemical staining using labeled streptavidin-biotin (LSAB) and HE-staining were performed. In the immunohistochemical staining, anti-MAdCAM-1 and anti-β7integrin were used as primary antibodies and biotin-labeled FITC was employed as a secondary antibody.

B. Results and Discussion

Figure 2:
FIG. 2 shows the results of HE staining, demonstrating the effect of DHNA administration on colonic mucosa of DSS colitis rats.

The survival rate of the DHNA administration group on day 10 after starting the test was significantly high (FIG. 1). Findings of the HE-staining included the following: In the control group, ulcer and erosion were found in the epithelium, and cellular infiltration and submucosal thickening were found. In contrast, in the DHNA administration group, suppression of the above conditions was observed (FIG. 2).

Figure 3A:
FIGS. 3A and 3B show the results of immunohistochemical staining of β7 positive cells of DSS enteritis rats.
Figure 3B:
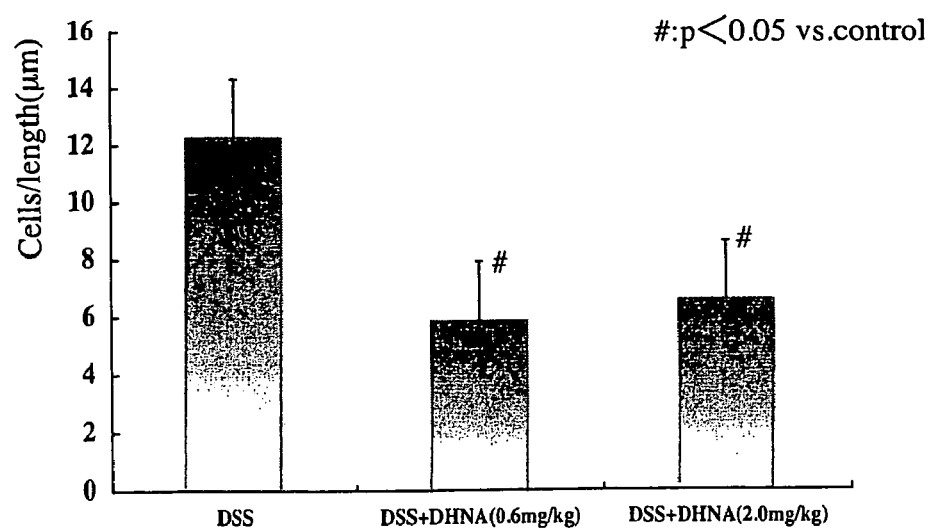
Figure 4A:
FIGS. 4A and 4B show the effect of DHNA on expression of an adhesion molecule MAdCAM-1 in DSS colitis rats.
Figure 4B:
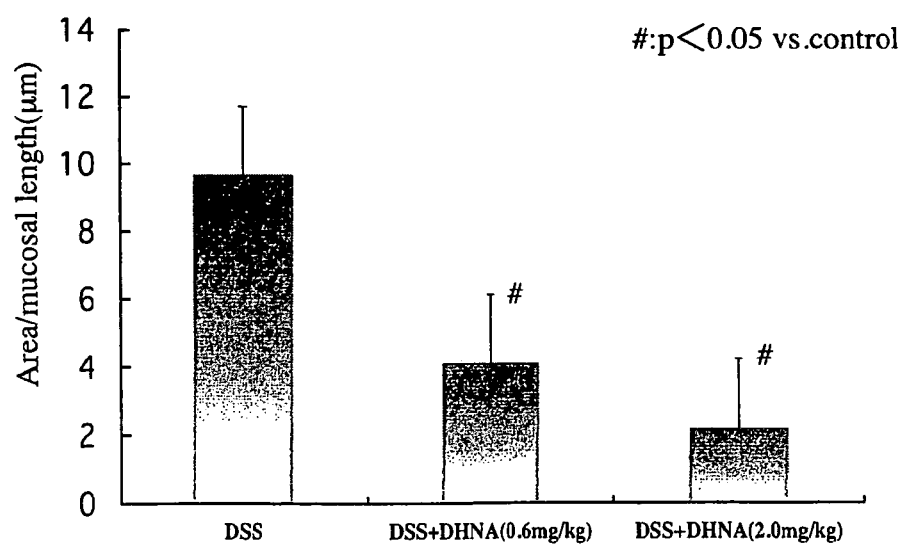

The above immunohistochemical staining revealed that the DHNA administration group had reduced β7 positive cells (FIGS. 3A and 3B). Also, in the DHNA administration group, expression of adhesion molecule MAdCAM-1 was found to be suppressed (FIGS. 4A and 4B).

From the above results, DHNA has been found to suppress development of DSS enteritis by mediation through suppressing infiltration of activated immunocytes.

What is claimed is:

1. A method for treating an inflammatory bowel disease comprising:
   administering to a subject in need thereof an effective amount of 1,4-dihydroxy-2-naphthoic acid or a salt thereof.

2. The method of claim 1, wherein said disease is ulcerative colitis.

3. The method of claim 1, wherein said disease is Crohn's disease.

4. The method of claim 1, wherein said disease is not ulcerative colitis or Crohn's disease.

5. The method of claim 1, wherein the 1,4-dihydroxy-2-naphthoic acid or a salt thereof is administered in a food or beverage.

6. The method of claim 1, wherein pure 1,4-dihydroxy-2-naphthoic acid or a salt thereof is administered.

7. The method of claim 1, wherein a daily dose of 1 to 100 mg of 1,4-dihydroxy-2-naphthoic acid or a salt thereof is administered.

8. A method for treating an inflammatory bowel disease characterized by mucosal inflammation or by invasion of activated immunocytes comprising:
   administering to a subject in need thereof an effective amount of 1,4-dihydroxy-2-naphthoic acid or a salt thereof.

9. The method of claim 8, wherein said disease is ulcerative colitis.

10. The method of claim 8, wherein said disease is Crohn's disease.

11. The method of claim 8, wherein the 1,4-dihydroxy-2-naphthoic acid or a salt thereof is administered in a food or beverage.

12. The method of claim 8, wherein 1,4-dihydroxy-2-naphthoic acid is administered.

13. The method of claim 8, wherein a salt of 1,4-dihydroxy-2-naphthoic acid is administered.

14. The method of claim 8, wherein said disease is characterized by epithelial ulceration or erosion, or by submucosal cellular infiltration and submucosal thickening.

* * * * *